United States Patent
Wang et al.

(10) Patent No.: US 6,458,867 B1
(45) Date of Patent: Oct. 1, 2002

(54) HYDROPHILIC LUBRICANT COATINGS FOR MEDICAL DEVICES

(75) Inventors: Lixiao Wang, Maple Grove; Dachuan Yang; John Jianhua Chen, both of Plymouth; Yiqun Bruce Wang, Maple Grove; Lance A. Monroe, New Hope; Joel R. Munsinger, Albertville, all of MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/406,987

(22) Filed: Sep. 28, 1999

(51) Int. Cl.$^7$ ................................................ A01N 1/00
(52) U.S. Cl. .................. 523/105; 523/112; 523/113; 604/265; 606/108; 623/1.11
(58) Field of Search .................. 604/265; 606/108; 623/1.11; 523/105, 112, 113

(56) References Cited

U.S. PATENT DOCUMENTS

| | | | |
|---|---|---|---|
| 2,814,296 A | 11/1957 | Everett | 128/339 |
| 3,566,874 A | 3/1971 | Sheperd et al. | 128/349 |
| 3,826,674 A | 7/1974 | Schwarz | 117/62.2 |
| 4,026,296 A | 5/1977 | Stoy et al. | 128/349 B |
| 4,100,309 A | 7/1978 | Micklus et al. | 427/2 |
| 4,248,685 A | 2/1981 | Beede et al. | 204/157.22 |
| 4,323,071 A | 4/1982 | Simpson et al. | 128/343 |
| 4,373,009 A | 2/1983 | Winn | 428/424.2 |
| 4,445,509 A | 5/1984 | Auth | 128/305 |
| 4,447,590 A | 5/1984 | Szycher | 528/76 |
| 4,459,318 A | 7/1984 | Hyans | 427/36 |
| 4,495,312 A | 1/1985 | Hata et al. | 523/105 |
| 4,588,398 A | 5/1986 | Daugherty et al. | 604/265 |
| 4,592,920 A | 6/1986 | Murtfeldt | 427/2 |
| 4,636,346 A | 1/1987 | Gold et al. | 264/139 |
| 4,720,521 A | 1/1988 | Spielvogel et al. | 524/862 |
| 4,876,126 A | 10/1989 | Takemura et al. | 428/35.7 |
| 4,901,707 A | 2/1990 | Schiff | 128/1 D |
| 4,936,310 A | 6/1990 | Engström et al. | 128/673 |
| 4,990,134 A | 2/1991 | Auth | 604/22 |
| 5,026,607 A | 6/1991 | Kiezulas | 428/423.7 |
| 5,032,113 A | 7/1991 | Burns | 604/96 |
| 5,041,100 A | 8/1991 | Rowland et al. | 604/265 |
| 5,066,285 A | 11/1991 | Hillstead | 604/164 |
| 5,071,649 A | 12/1991 | Hunter | 424/78.38 |
| 5,084,315 A | * 1/1992 | Karimi et al. | 428/366 |
| 5,089,260 A | 2/1992 | Hunter et al. | 424/78.38 |
| 5,091,205 A | 2/1992 | Fan | 427/2 |
| 5,100,381 A | 3/1992 | Burns | 604/96 |
| 5,135,487 A | 8/1992 | Morrill et al. | 604/96 |
| 5,135,516 A | 8/1992 | Sahatjian et al. | 604/265 |
| 5,209,730 A | 5/1993 | Sullivan | 604/96 |
| 5,229,211 A | 7/1993 | Murayama et al. | 428/424.4 |
| 5,266,359 A | 11/1993 | Spielvogel | 427/388.4 |
| 5,272,012 A | 12/1993 | Opolski | 428/423.1 |
| 5,331,027 A | * 7/1994 | Whirtbourne | 524/37 |
| 5,334,169 A | 8/1994 | Brown et al. | 604/282 |
| 5,441,488 A | 8/1995 | Shimura et al. | 604/265 |
| 5,443,457 A | 8/1995 | Ginn et al. | 604/280 |
| 5,466,230 A | 11/1995 | Davila | 604/256 |
| 5,503,631 A | 4/1996 | Onishi et al. | 604/96 |
| 5,509,899 A | 4/1996 | Fan et al. | 604/96 |
| 5,531,715 A | 7/1996 | Engelson et al. | 604/265 |
| 5,534,007 A | 7/1996 | St. Germain et al. | 606/108 |
| 5,599,305 A | 2/1997 | Hermann et al. | 604/95 |
| 5,647,846 A | 7/1997 | Berg et al. | 604/93 |
| 5,651,781 A | 7/1997 | Grace | 606/1 |
| 5,653,695 A | 8/1997 | Hopkins et al. | 604/265 |
| 5,670,558 A | 9/1997 | Onishi et al. | 523/112 |
| 5,688,747 A | 11/1997 | Khan et al. | 508/208 |
| 5,688,855 A | 11/1997 | Stoy et al. | 524/505 |
| 5,693,034 A | 12/1997 | Buscemi et al. | 604/265 |
| 5,702,364 A | 12/1997 | Euteneuer et al. | 604/96 |
| 5,712,229 A | 1/1998 | Hopkins et al. | 508/202 |
| 5,749,837 A | 5/1998 | Palermo et al. | 600/585 |
| 5,769,830 A | 6/1998 | Parker | 604/282 |
| 5,772,669 A | 6/1998 | Vrba | 606/108 |
| 5,792,124 A | 8/1998 | Horrigan et al. | 604/282 |
| 5,792,415 A | 8/1998 | Hijlkema | 264/530 |
| 5,800,412 A | 9/1998 | Zhang et al. | 604/280 |
| 5,807,404 A | 9/1998 | Richter | 623/1 |
| 5,824,359 A | 10/1998 | Khan et al. | 427/2.3 |
| 5,836,964 A | 11/1998 | Richter et al. | 606/194 |
| 5,837,313 A | 11/1998 | Ding et al. | 427/2.21 |
| 5,843,120 A | 12/1998 | Israel et al. | 606/198 |
| 5,849,368 A | 12/1998 | Hostettler et al. | 427/536 |
| 5,889,073 A | 3/1999 | Zhang et al. | 522/3 |
| 5,919,570 A | 7/1999 | Hostettler et al. | 428/424.8 |
| 5,925,074 A | 7/1999 | Gingras et al. | 623/1 |
| 6,046,143 A | 4/2000 | Khan et al. | 508/208 |
| 6,071,266 A | 6/2000 | Kelley | 604/265 |

FOREIGN PATENT DOCUMENTS

| | | |
|---|---|---|
| EP | 0 380 102 A1 | 1/1990 |
| WO | 91/08790 | 6/1991 |
| WO | 95/29722 | 11/1995 |
| WO | 99/38545 | 8/1999 |
| WO | 99/44665 | 9/1999 |

OTHER PUBLICATIONS

Szycher, Ph.D., Michael, "Biostability of Polyurethane Elastomers: A Critical Review", *Blood Compatible Materials and Devices*, Chapter 4, pp. 33–85 (1991).
Release Agents, vol. 14, pp. 411–420.
Drag Reduction, vol. 5, pp. 129–151.
Lubrication and Lubricants, vol. 15, pp. 463–517.
Product Brochure: Tecoflex.
Product Brochure: Gantrez® AN Copolymer.

* cited by examiner

*Primary Examiner*—Edward J. Cain
(74) *Attorney, Agent, or Firm*—Vidas, Arrett & Steinkraus P.A.

(57) ABSTRACT

The present invention relates to a medical device comprising at least one tubular member having an inner surface and an outer surface. The inner surface of the tubular member is at least occasionally subjected to contact with at least one second surface. The tubular member therefore comprises a hydrophilic lubricious coating disposed on its inner surface to reduce the friction between the inner surface of the tubular member and the second surface which is caused by movement.

38 Claims, 8 Drawing Sheets

HYDROPHILIC LUBRICANT COATINGS FOR MEDICAL DEVICES

FIELD OF THE INVENTION

This invention relates to a water soluble lubricious coating for a medical device such as a catheter assembly.

BACKGROUND OF THE INVENTION

Catheters are used in surgical procedures for insertion into blood vessels, urethra, or body conduits during such procedures as coronary angioplasty, stent delivery and placement for the opening of occluded or blocked blood vessels, for urological and reproductive surgeries, and to deliver biologically compatible fluids, such as radiologically opaque fluid for contrast x-rays to precise locations within the body.

Depending on the procedure involved, catheters may be one of several different types including an over the wire, a single operator exchange or a fixed wire catheter assembly.

Over the wire catheters may be used as guide catheters during coronary angioplasty, for instance. The guide catheter provides access to the area in which the stenosis or blockage may be found, and provides support for the treatment catheter which often includes a balloon dilatation system wherein a dilatation balloon is delivered to a site of stenosis in an artery and is used to alleviate the stenosis.

In operation, the guide catheter is introduced over a guide wire through a previously placed introducer sheath and advanced through a blood vessel to the location of a stenosis. The guide wire can then be removed.

Other procedures may involve the introduction of other medical devices at precisely specific bodily locations including the delivery of stents, stent-grafts, grafts, vena cava filters, other expandable medical devices, and so forth.

During these procedures, the catheters must be able to traverse tortuous pathways through blood vessels to the stenosis in a manner as atraumatic to the patient as possible. It is therefore desirable to make insertion through the patient in such a way to limit the insertion time and discomfort as much as possible.

A common problem which occurs in catheter assemblies is friction or adhesion between various parts which periodically come into contact with one another during the medical procedure. For instance, friction can occur between the guide catheter and guide wire, between the introducer sheath and the guide catheter, or between the guide catheter and the balloon catheter, for instance, and may increase the difficulty of insertion, cause loss of catheter placement, and result in discomfort or damage to the patient. It is therefore desirable to improve the moving relationship between the various parts of the catheter assemblies.

The materials from which catheters are produced are typically polymeric or metallic in nature, and in general, are inherently non-lubricious. When these non-lubricious materials come into contact, friction occurs. Medical device manufacturers have used various approaches to reduce the coefficient of friction between these surfaces.

Hydrophobic coatings have been used to impart lubricity to medical devices including silicone based lubricants, glycerine or olive oil. These coatings have been known to wash off when exposed to an aqueous environment, lose initial lubricity rapidly, and lack abrasion resistance. Residual amounts of silicone have also been known to cause tissue reaction and irritation in patients. The loss of lubricity can lead to discomfort during insertion into a patient, and damage to blood vessels and tissues due to frictional forces during insertion or removal of the device. Examples of silicone based lubricants include polysiloxanes and modified polysiloxanes. Often they include a polar group which may be an aminoalkyl or carboxyalkyl terminating group. U.S. Pat. No. 5,084,315 to Karimi et al. issued Jan. 28, 1992 discusses the problems with migration and beading.

U.S. Pat. No. 5,266,359 to Spielvogel issued Nov. 30, 1993 describes a lubricating composition for a medical device which includes an emulsion of a noncuring polysiloxane, a surfactant and water. The surfactants are copolymers of polysiloxane and polyoxyethylene which are reactive and when cured, adhere to the surface. While Spielvogel teaches a method of application which does not utilize solvent, the problems associated with silicone based lubricants remain.

U.S. Pat. No. 5,272,012 to Opolski issued Dec. 21, 1993 describes a method for providing a medical apparatus with a protective lubricious coating comprising providing a coating solution which contains a protective compound such as a urethane, a slip additive such as a siloxane, and optionally, a crosslinking agent for the protective compound such as polyfunctional aziridine, coating the solution onto a surface of a medical apparatus and allowing the coating to set. The protective compound binds the slip additive such that domains of the slip additive are exposed in the formed layer. The coating solution may also contain a crosslinking agent. The protective compound binds the slip additive such that domains of the slip additive are exposed in the formed layer. The coating solution may also contain a crosslinking agent. The protective compound preferably has functional moieties capable of crosslinking to other moieties within the protective compound and with moieties derived from the medical device.

Another approach for reducing the coefficient of friction is to add a layer of a low friction material such as polytetrafluoroethylene, hereinafter PTFE and commonly known by the tradename of Teflon®. For instance, PTFE may be added as an inner layer of an internal catheter lumen to reduce friction between the guide catheter and the treatment catheter, for instance. The problem with the use of this inner layer of PTFE is that it requires a separate extrusion process, and also requires etching. Adhesion is also generally a problem between the PTFE and the polymeric catheter material as well. U.S. Pat. No. 5,647,846 to Berg et al. solved these problems through the use of a geometrically configured inner surface of the inner layer of a guide catheter, achieving low friction properties through geometry, rather than through the use of a lubricious polymer, thereby eliminating the need for the lubricious polymer. Berg et al. however, discusses forming the inner layer of a lubricious polymer, such as PTFE, or alternatively, coating the inner surface with a lubricant such as silicone.

Hydrophilic compounds have also been used to impart lubricity in medical devices. Such compounds are biocompatible or blood compatible, and are more readily discharged from the body and have less of a tendency to cause tissue irritation. However, because of the hydrophilicity, It is also more difficult to retain such coatings on the surface of the medical device throughout the procedure. U.S. Pat. No. 5,509,899 to Fan et al. issued Apr. 23, 1996 describes a lubricious coating for a medical balloon and catheter wherein the balloon is tightly wrapped and folded upon itself tortuously and tightly so that when in contact with each other for insertion into the body, the balloon is free of bridging and adhesion between abutting surfaces. The balloon has a base of a continuous polymeric surface which is expandable from a folded, wrapped configuration with surfaces touching each other. Examples of such polymeric materials include Nylon, Selar®, polyethylene terephthalate, polyethylene or similar materials. These materials may provide excellent balloon stock but are not necessarily sufficiently lubricious to be used by themselves. Therefore, a lubricious, biocompatible hydrogel coating is disposed on the polymeric surface and a thin, lubricious, blood-compatible coating is disposed upon the hydrogel coating and adheres to it to prevent abutting surfaces of folded polymer surfaces from adhering to each other during inflation and also to prevent delamination of the hydrogel coating and/or rupture of the balloon. The blood-compatible coating is polyethylene glycol, methoxy polyethylene glycol or mixtures thereof having a molecular weight between about 100 and 20,000 grams per mole.

U.S. Pat. No. 5,849,368 to Hostettler et al. issued Dec. 15, 1998 describes a process for rendering the surfaces of polymeric plastic or rubber materials, which are intrinsically non-polar or only slightly polar, polar or more polar, and hydrophilic, so that amine-containing functional groups, and ultimately, a durable tenaciously adhering, slippery polyurethane or polyurethane-urea hydrogel coating may subsequently be applied to the polymer surface. The process involves dual plasma-treatment of a polymeric plastic or rubber substrate material such that amine and amino groups are affixed to the substrate surface to make it more hydrophilic and reactive toward the terminal isocyanate groups of the polyurethane or polyurethane/urea prepolymers.

Although each of these methods describes a way in which the coefficient of friction may be reduced, a need still exists for a simple, easy to apply coating which is lubricious and biocompatible, and which has good retention on the surface of the device.

The present inventors have found a hydrophilic lubricant coating for medical devices, and in particular for catheter assemblies, to render inherently non-lubricious surfaces, lubricious, and a method for coating such devices which involves coating the inner surface a tubular member of a medical device. This hydrophilic lubricant coating overcomes the aforementioned problems associated with conventional lubricious coatings, and the problems associated with the use of silicone based lubricants and the addition of polytetrafluoroethylene layers.

SUMMARY OF THE INVENTION

This invention relates to a coating for rendering a medical device lubricious. The coating comprises pretreating primer composition, and a hydrophilic lubricious coating. The primer compound comprises substituents that are capable of adhering or bonding to, and improving the retention of the hydrophilic lubricant to the surface of the medical device. One such mechanism through which the primer compound may retain the hydrophilic polymer, is through hydrogen bonding.

This invention further relates to a medical device comprising at least one tubular member having an inner surface and an outer surface. The inner surface of the tubular member is at least occasionally subjected to contact with at least one second surface. The tubular member further comprises a hydrophilic coating disposed on the inner surface. The hydrophilic coating is present to inhibit the inner surface of the tubular member and the second surface from adhering to each other, and reduces the friction caused by movement between the two surfaces. The inner surface may first be pretreated with the primer composition.

The tubular member preferably comprises at least one thermoplastic polymer and the second surface preferably comprises a metal.

The hydrophilic coating may be coated on the inner surface of the tube by injection, or coextrusion.

This invention further relates to a catheter assembly comprising at least one polymeric sheath having an inner surface and an outer surface. The inner surface of the first polymeric sheath is at least occasionally subjected to contact with at least one second surface, and comprises a water soluble coating disposed on the inner surface of the polymeric sheath. The hydrophilic coating is present to inhibit the inner surface and the second surface from adhering to each other.

The polymeric sheath comprises at least one thermoplastic polymeric material. The second surface to which the inner surface of the polymeric sheath comes into contact may be a polymeric material or a metal.

The inner surface of the polymeric sheath may first be coated with a primer of a crosslinkable composition which is readily wettable. This improves the uniformity and shelf stability of the lubricious coating. The water soluble lubricious coating may further comprise Vitamin E to further improve the shelf stability of the coating.

The present invention further relates to a stent deployment catheter assembly having at least one tubular member for retention and release of a stent. The tubular member may be a retractable sheath, or it may be at least one stent retaining sleeve. A hydrophilic lubricious coating is disposed on the inner surface of the tubular member in order to facilitate stent release by reducing the coefficient of friction between the tubular member and the stent.

The lubricious coating of the present invention provides improved lubricity, eliminates migration problems associated with oil based lubricants and eliminates tissue reaction and irritation associated with oil based silicone lubricants.

Furthermore, due to the excellent lubricity, the diameter of the outer sheath of a medical device may be decrease thereby improving performance.

DETAILED DESCRIPTIONS OF THE PREFERRED EMBODIMENTS

Figure 3:
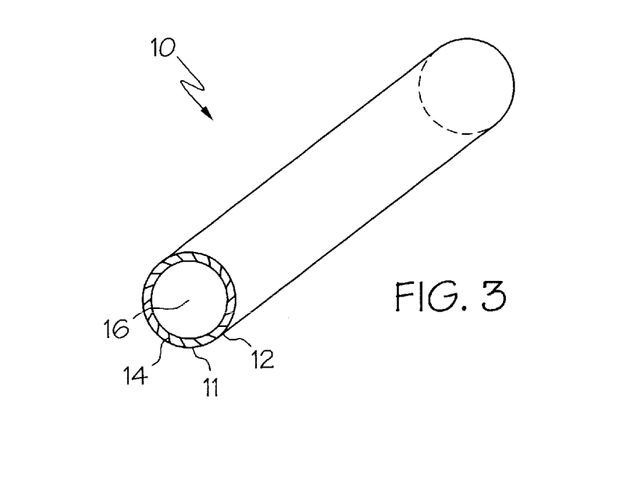
FIG. 3 shows generally a tubular member having coated on its inner surface, the hydrophilic coating of the present invention.

FIG. 3 illustrates generally at (10) a tubular member which may be utilized in a medical device. The tubular member comprises an outer surface (12), and an inner surface (14), the inner surface forming a lumen (16). The lumen may be, for instance, a guide wire lumen for a catheter which is used in surgical procedures such as coronary angioplasty, stent delivery and placement for the opening of occluded or blocked blood vessels, for urological and reproductive surgeries, and to deliver biologically compatible fluids, such as radiologically opaque fluid for contrast x-rays to precise locations within the body.

A water soluble lubricious coating (11) is disposed on the inner surface (14) of the tubular member (10). The coating reduces the coefficient of friction between the tubular member and any surface with which it comes into contact, and which are in a moving or sliding relationship with one another. The tubular member may be comprised of a polymeric material for instance, which is inherently non-lubricious. The tubular member may form any type of catheter including balloon catheters and stent delivery catheters, retractable sheaths or stent retaining sleeves for stent delivery catheters, guide wire lumens, pull wire lumens, and so forth.

Figure 4:
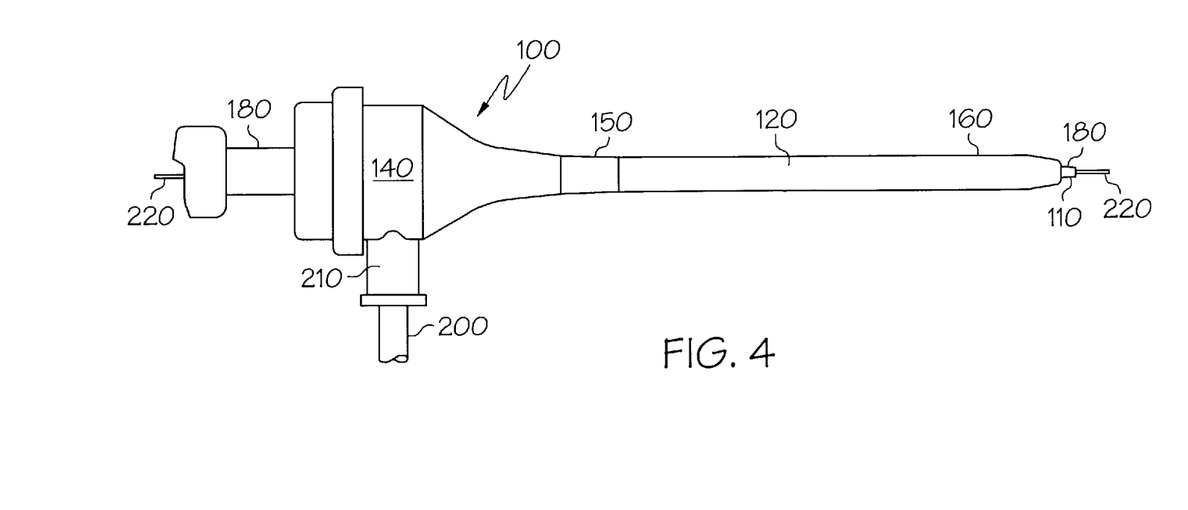
FIG. 4 shows a side view of a catheter sheath introducer having a hydrophilic coating on the inner surface of the tubular sheath of the catheter sheath introducer.

FIG. 4 illustrates generally at 100 a catheter introducer having a tubular sheath (120) and a hub (140) attached to the proximal end (150) of tubular sheath (120). A branch conduit (200) and a locking sleeve (210) is provided to allow for, among other things, connections to saline solution or medicines and access to other medical procedures. A guide wire (220) is shown as it is often used with such devices as balloon angioplasty catheters. A dilator unit is shown at (180). Hydrophilic coating (110) is disposed on the inner surface of tubular sheath (120) for inserting and guiding a catheter into living tissue.

A core wire may first be inserted through a hollow needle which is placed through the skin into the lumen of the desired blood vessel. The catheter introducer which comprises the tubular sheath (120), and a removable hollow stylet or dilator unit (180) may be advanced together over the core wire into the vessel. The core wire and dilator unit are then removed, leaving only the tubular sheath (120) of the catheter introducer present in the vessel. A catheter may then be advanced through the tubular sheath (120), into an artery for conventional purposes of angioplasty or any other desired purpose.

The tubular sheath (120) may therefore come into contact with a core wire (220), dilator unit and catheter (180). The hydrophilic coating (110) on the inner surface of the tubular sheath (120) reduces the friction between the tubular sheath and the medical apparatus with which it comes into contact. These tubular sheaths may be utilized to maneuver medical devices such as catheter delivery devices for dilatation balloons, stents, stent-grafts, grafts, vena-cava filters, or other such devices to the desired location.

Catheter sheath introducer (100) is typical of current, commercially available introducers but many modifications can be made. Proximal end (150) of sheath (120) may, for instance, be made of a rigid material while distal end (160) of sheath (120) may be made of flexible material for better control outside the body by the physician, for instance.

Introducer type devices are known in the art and there are a vast number of different embodiments of such devices for which the present invention would find utility. Introducer type devices are illustrated in U.S. Pat. No. 5,066,285 issued Nov. 19, 1991 to Hillstead and in U.S. Pat. No. 5,466,230 issued Nov. 14, 1995 to Davila incorporated by reference herein.

Figure 5:
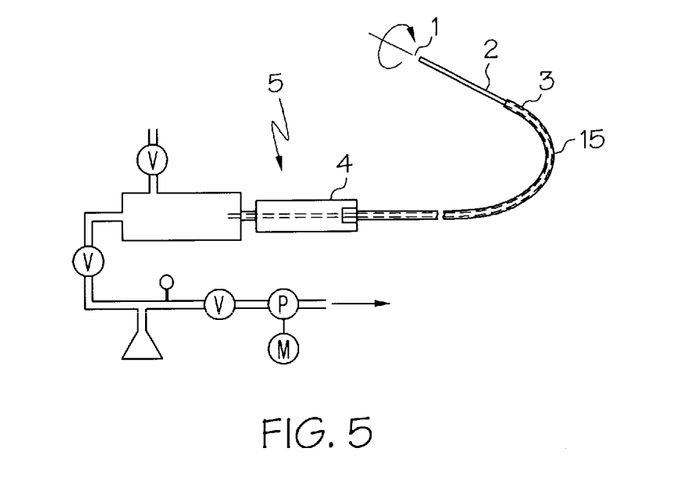
FIG. 5 shows a side view of a medical device used for passing a high-rotational-speed cutting tool into a vessel to remove abnormal deposits having the hydrophilic lubricious coating of the present invention disposed on the inner surface of guiding catheter.

FIG. 5 illustrates generally at (5), one embodiment of a medical device used for passing a high-rotational-speed cutting tool into a vessel to remove abnormal deposits. The cutting tool (1) is mounted at the end of a flexible drive shaft which transmits torque from a torque-generating device (4), such as an electric or pneumatic motor. The drive shaft (2) is surrounded for most of its length by a guiding catheter.

Another embodiment in which the present invention may be utilized is in a surgical cutting device illustrated in U.S. Pat. No. 5,651,781 issued Jul. 29, 1997 to Grace, incorporated by reference herein. The outer sheath in Grace houses a surgical cutting apparatus including a hollow cylindrical cutting blade member. The blade may be extended and retracted.

In order to provide a low-friction passage of rotational motion between the drive shaft (2) and the guiding catheter (3), the inner surface of the guiding catheter (3) may be coated with the lubricious coating of the present invention (15). Such devices are described in detail in U.S. Pat. No. 4,445,509 issued May 1, 1984 and in U.S. Pat. No. 4,990,134 issued Feb. 5, 1991, both to Auth, herein incorporated by reference.

The coatings of the present invention may be incorporated into both over-the-wire (OTW) catheters and rapid-exchange (RX) or single operator catheters. These types of catheter construction are also used in stent deployment catheters.

Figure 6:
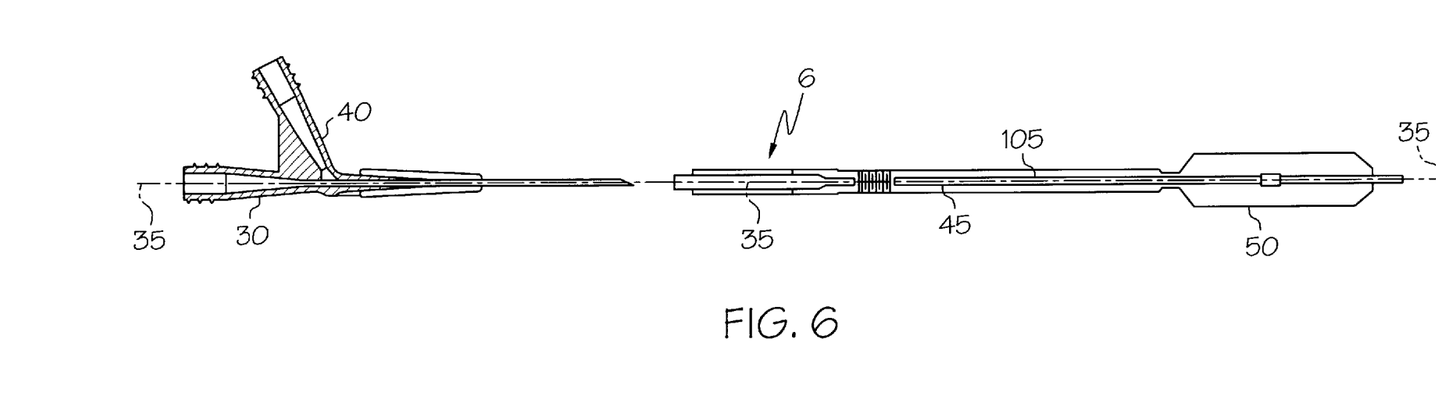
FIG. 6 shows a side view of an over-the-wire catheter device specifically designed as a dilatation catheter for an inflatable balloon having the lubricious coating of the present invention disposed on the inner surface of the guide wire lumen.

FIG. 6 illustrates generally at (6) an over-the-wire catheter device specifically designed as a dilatation catheter for an inflatable balloon (50) which device comprises a manifold system designated generally at (30). The manifold (30) may further comprise a inflation luer (40). Guide wire (35) extends through the guide wire lumen (45) which is coated on the inner surface with the lubricious coating of the present invention (105), for reducing the wire movement frictional force, thereby improving the sliding relationship, between the guide wire (35) and the inner surface of the guide wire lumen (45). The guide wire lumen (45) encloses the guide wire (35), which aids in the navigation of the catheter (6) through the appropriate vessel.

Figure 7:
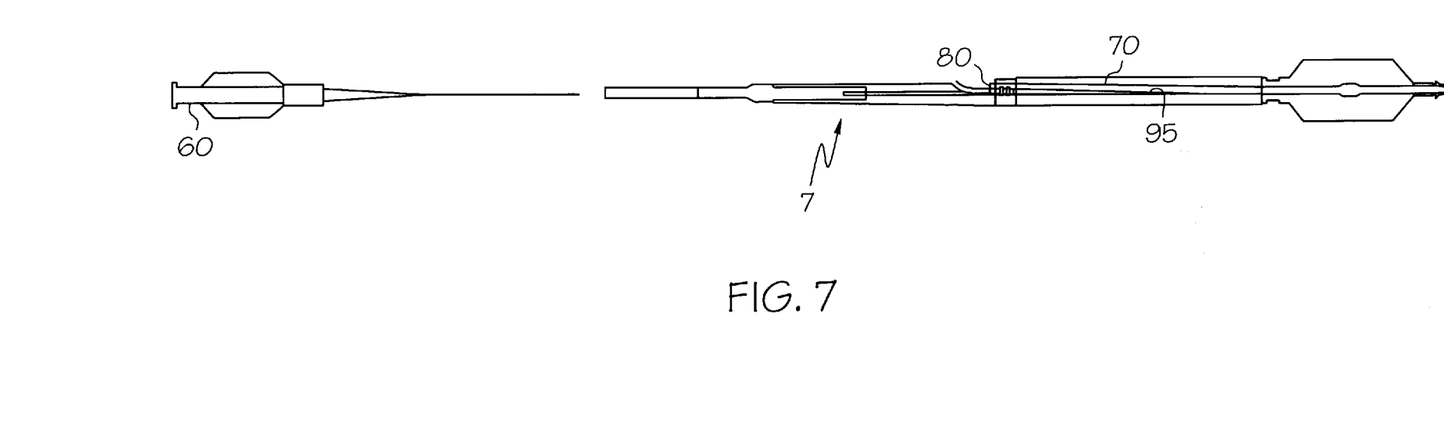
FIG. 7 shows a rapid exchange embodiment of a balloon catheter device which is similar in construction to the catheter device shown in FIG. 6.

FIG. 7 illustrates generally at (7) a rapid exchange embodiment of a balloon catheter device which is similar in construction to the catheter device shown in FIG. 6. The inner surface of the guide wire lumen (70), including the port (80) of the guide wire lumen, is coated with the lubricious coating of the present invention (95) to reduce wire movement friction when a guide wire is introduced into port (80), and is advanced through the guide wire lumen (70).

The coatings of the present invention may also be utilized in stent deployment catheter systems as well as in angioplasty balloon catheters. In the case of a stent deployment catheter system, balloons may be utilized to expand the stent once it is in position for deployment, or the stent may be self-expanding. Retractable sheaths may be utilized wherein the sheath is moved over the stent once it is in position. The retractable sheath may act both to protect the stent, as well as to prevent it from expanding prematurely. Once the sheath is retracted, the stent can expand. The coatings of the present invention may also be utilized as a coating on the inner surface of the retractable sheath, for instance.

Stent deployment catheter devices, including those having a retractable sheath, are described in U.S. Pat. No. 5,534,007 issued Jul. 9, 1996 to St. Germain et al., herein incorporated by reference.

Figure 8:
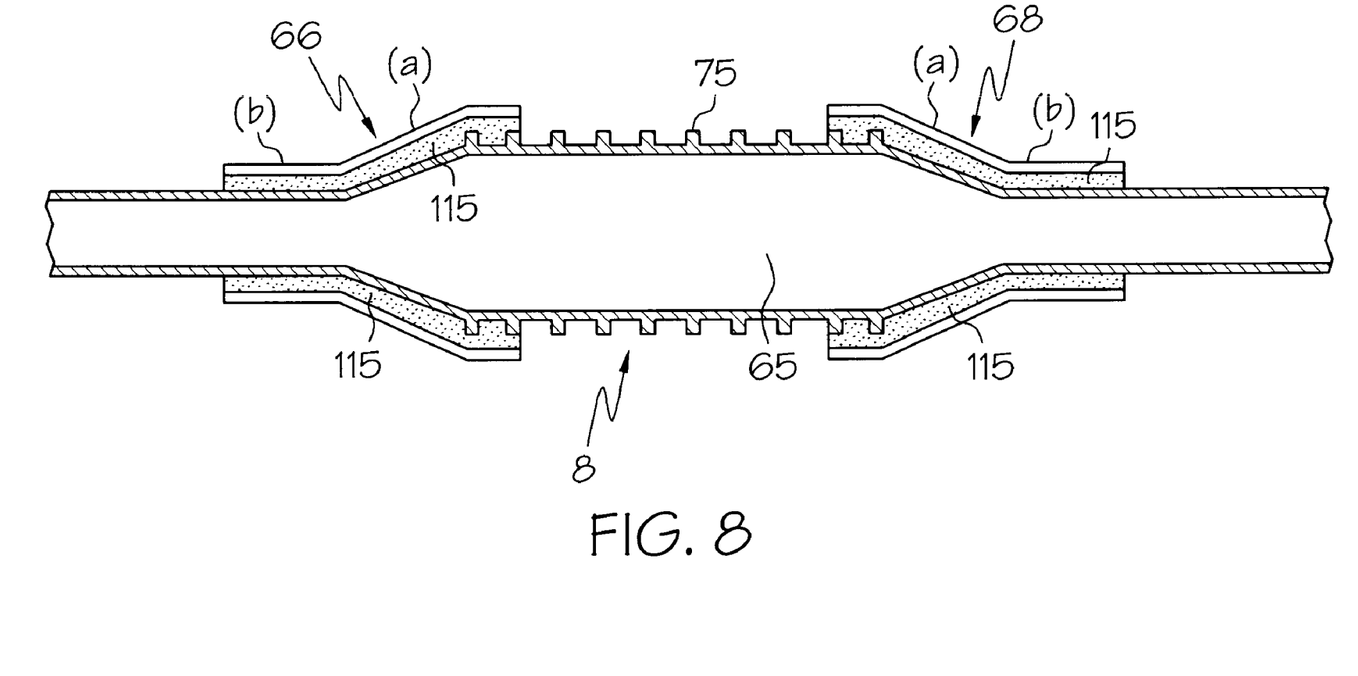
FIG. 8 shows a side view of a stent delivery catheter utilizing an inflatable balloon for releasing the stent. The lubricious coating of the present invention is disposed on the inner surface of the stent retaining sleeves.

FIG. 8 shows generally at (8) a sideview of a stent delivery catheter assembly. In this embodiment, catheter (8) has an expandable portion or balloon (65). Disposed about the balloon (65) is a stent (75). Stent (75) may be any type of stent capable of being delivered by a stent delivery catheter, and may be self-expanding, or may be balloon expandable. In this embodiment, the stent (75) is balloon expandable.

Attached to the catheter are a pair of stent retaining sleeves (66) and (68). The sleeves each include a first portion (a) and a second portion (b). When balloon (65) is in a non-inflated state, the first sleeve portions (a), overlay the ends of balloon (65) as well as the ends of stent (75), holding the stent in position. Regardless of the inflated or non-inflated state of balloon (65), the second sleeve portions (b), are fixedly attached to catheter (8). When balloon (65) is inflated, stent (75) releases from sleeve portions (66a) and (68a).

Stent retaining sleeves (66) and (68) may be formed of many different polymeric materials. These polymeric materials are typically inherently non-lubricious. Stent (75) is typically a metal such as a metal alloy of nickel and titanium. For reducing the coefficient of friction, and improving the sliding relationship between retaining sleeves (66) and (68), and stent (75), the lubricious coating of the present invention (115) is disposed on the inner surface of the pair of sleeves (66) and (68).

Figure 9:
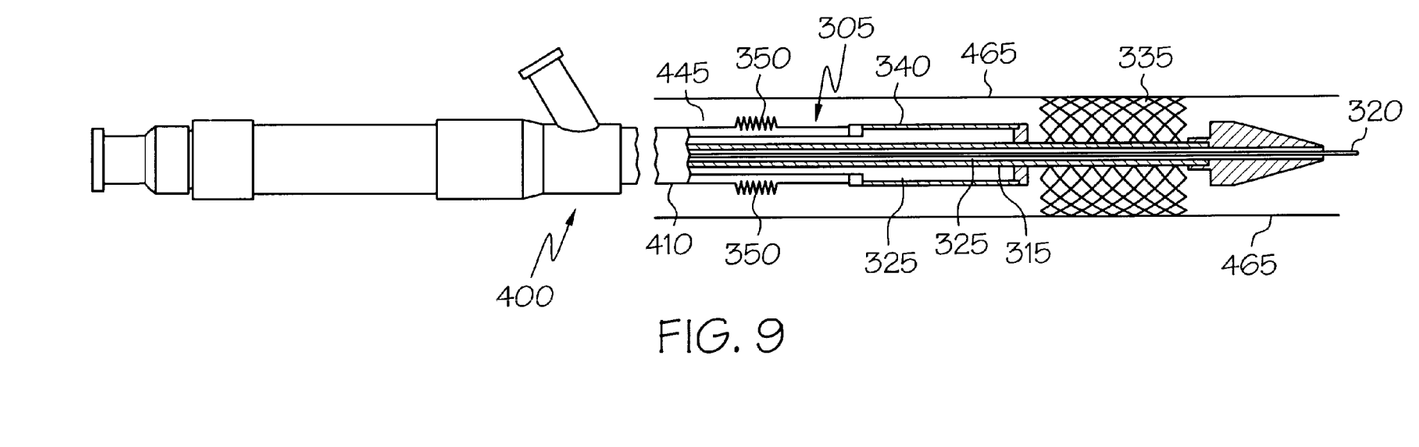
FIG. 9 shows a side view of a different embodiment of a stent delivery catheter with a loaded stent in the fully deployed position. This particular stent delivery catheter has retractable sheaths.

FIG. 9 shows generally at (400) a catheter delivery device having a self-expanding stent (335) in a fully deployed position. The device generally comprises a proximal outer (410) which is characterized by a flexible tube which contains a pull wire lumen and optionally a guide wire lumen (315). The outer (410) may be comprised of a polymeric material such as high density polyethylene (HDPE) or Surlyn®. Preferably, the guide wire lumen (315) encloses a guide wire (320) which aids in the navigation of the catheter (305) through the appropriate vessel. The guide wire lumen (315) may be made of a flexible, but incompressible construction such as a polymer encapsulated braid or coil. The lubricious coating (325) of the present invention may be disposed on inner surface of the guide wire lumen (315) to reduce the coefficient of friction between the guide wire (320) and the guide wire lumen (315).

This catheter delivery device has a distal sheath (340) which covers stent (335) when it is loaded. FIG. 9 illustrates distal sheath (340) in a fully retracted state and collapsible sheath (350) is in its compressed state thereby releasing the stent (335) to allow it to self-expand against the vessel wall (465). The hydrophilic coating (325) is disposed on the inner surface of the retractable sheath (340) to reduce the coefficient of friction between the retractable sheath (340) and the stent (335).

Further, the retractable distal sheath (340) which covers and contains the loaded stent (335), and holds the self-expanding stent (335) in its reduced delivery configuration, is connected to a retracting member (445). The retracting member (445) may be a rod, a cable, a tube which may also be used to transport fluids, a pull back wire, guide wire, or the like. The retracting member (445), e.g. a pull wire, extends longitudinally within the proximal outer (410), optionally through a retracting member lumen (not shown), such as an HDPE, nylon, or polyether block amide (Pebax®) tube. In a more specific embodiment, the retracting member lumen extends longitudinally through the proximal outer (410), and houses the pull back wire (445). The inner surface of the retracting member lumen may have disposed on its inner surface thereof, the lubricious coating of the present invention for reducing the coefficient of friction between the pull back wire (445) and the retracting member lumen.

Figure 10:
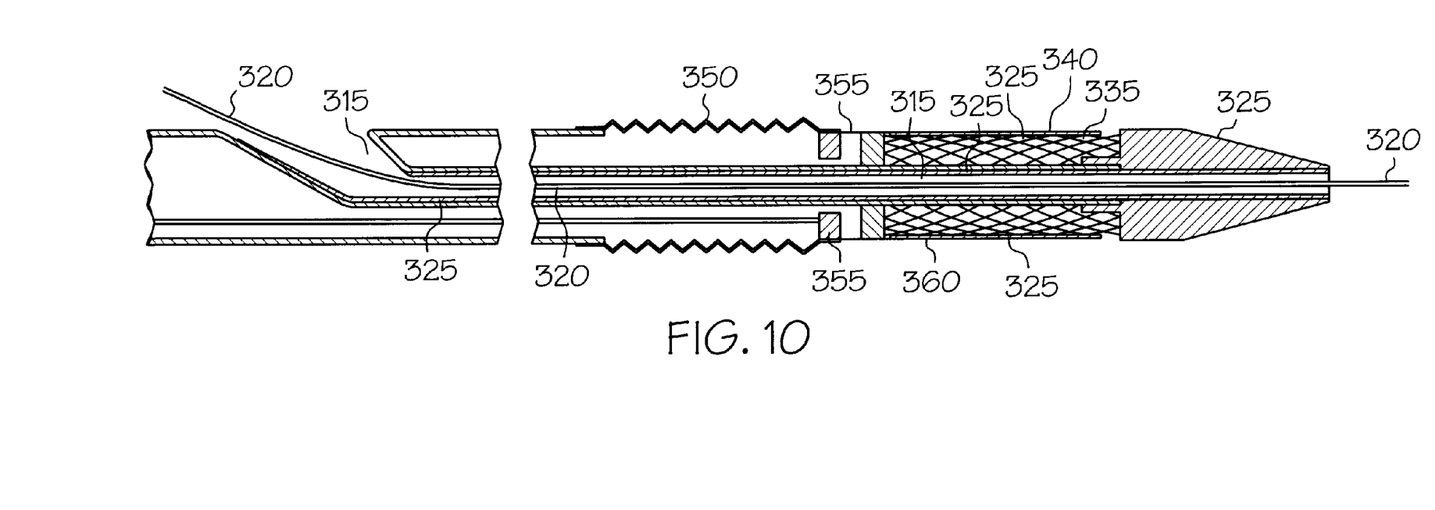
FIG. 10 shows a side view of a rapid exchange embodiment of a stent very similar in configuration to that shown in FIG. 9.

FIG. 10 illustrates a rapid exchange embodiment of a catheter delivery device which is similar in construction to that found in FIG. 9.

Figure 11:
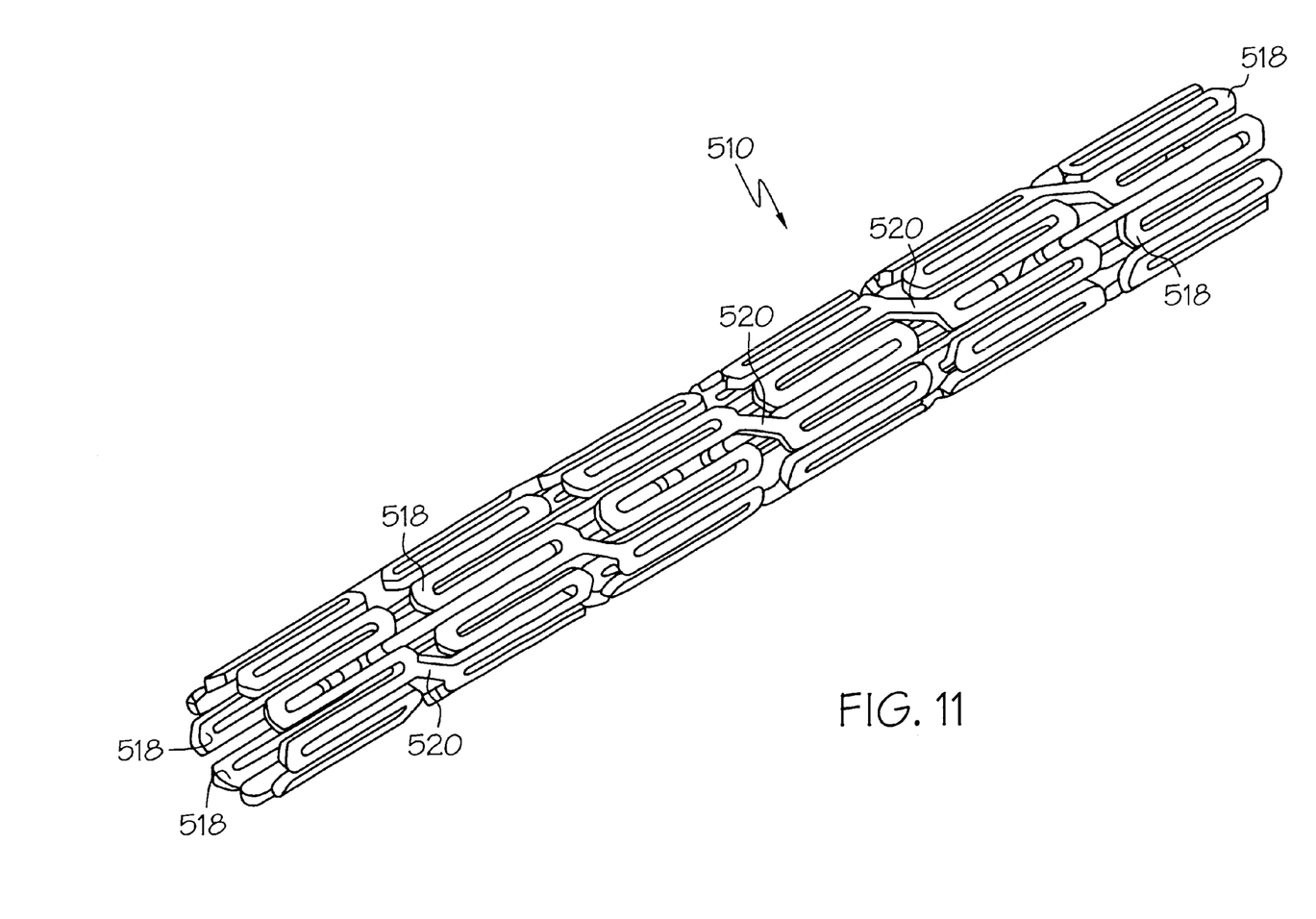
FIG. 11 illustrates a tubular, flexible, self-expanding stent shown in its unexpanded state.

FIG. 11 illustrates a tubular, flexible, self-expanding stent shown in FIG. 11 in an unexpanded state. The self-expanding stent shown in FIG. 11 may be used with either of the stent delivery catheters shown in FIG. 9 or FIG. 10. The retractable sheath (340) is pulled back with pull back wire (445) to release the stent. As shown in FIGS. 9 and 10, the lubricious coating (325) of the present invention is disposed on the inner surface of the retractable sheath (340) to reduce the coefficient of friction between the retractable sheath (340) and the stent for a smooth, easy release. These stents are described in detail in U.S. patent application Ser. No. 09/122,431 herein incorporated by reference.

Figure 12:
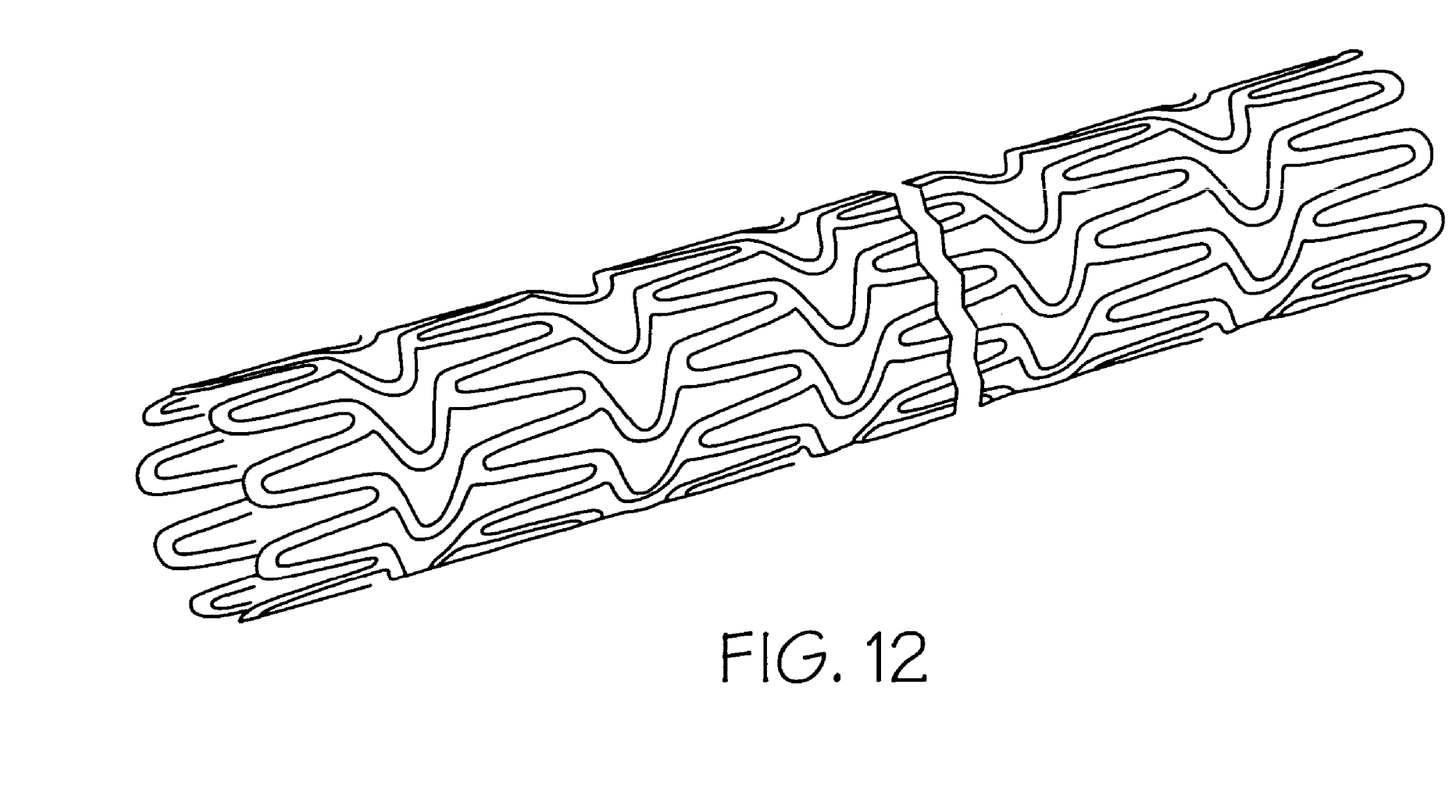
FIG. 12 illustrates a tubular, flexible, balloon-expandable stent shown in its unexpanded state.

FIG. 12 illustrates a balloon expandable stent which may be utilized with the balloon as shown in FIG. 8. As shown in FIG. 8, the lubricious coating of the present invention (115) is disposed on the inner surface of the pair of sleeves (66) and (68) to reduce the coefficient of friction between the stent retaining sleeves (66) and (68) and the stent for easier and smoother release of the stent. This type of stent is described in detail in U.S. Pat. No. 5,843,120, herein incorporated by reference.

Catheter devices such as those illustrated in FIG. 9 and FIG. 10 are explained more fully in detail in U.S. Pat. No. 5,534,007 to St. Germain et al. issued Jul. 9, 1996 and herein incorporated by reference.

In a preferred embodiment of the present invention, the hydrophilic lubricious coating (115) is a carboxylic acid, or alcohol, which has been converted from a nonhydrophilic polymeric material having, for instance, ester or amide groups capable of undergoing hydrolysis. Poly(maleic anhydride) may also be hydrolyzed to a carboxylic acid. In this embodiment, the polymeric material which forms the coating is coextruded simultaneously with the polymeric material used for forming sleeves (66) and (68). The sleeves may be formed from a variety of organic high polymer materials such as polyamide, polyester, polyvinyl chloride, polystyrene, polyacrylate, polymethacrylate, polyacrylonitrile, polyacrylamide, polyethylene, polypropylene, polyurethane, polyvinyl acetate, silicone resins, polytetrafluoroethylene (PTFE) and copolymers and blends thereof. The result is a two layered tubular construction wherein the inner layer is hydrophobic polyester or polyamide, and the outer layer is a polymeric material which may be any material listed above, as well as many others.

The inner layer of hydrophobic polyester or polyamide is then hydrolyzed either through acid or base catalysis, to a carboxylic acid, or alcohol. The result is a layer of hydrophilic lubricious coating. The sleeves are then cut from the tubular member resulting in a layered structure of hydrophilic coating on the inner surface and hydrophobic polymeric material on the outside.

The coatings of the present invention may be utilized to improve the deployment of any of stents, stent-grafts, grafts or vena cava filters, or other such expandable medical devices, by coating the inner surface of the polymeric sheath to reduce the friction between the sheath and the stent.

There are vast number of variations of catheter devices commercially available and the present inventors envision that the coating method described herein may be employed in any such device.

The devices discussed herein are meant only for illustration as to how the coatings of the present invention may be utilized, and are by no means intended as an exclusive list. One of skill in the art would understand how to incorporate the coatings and method of the present invention to any other such devices.

There are various types of hydrophilic polymers which may be useful to the present invention including both non-reactive and reactive. Hydrophilicity may also be obtained by the reaction of polymers in the presence of water which then subsequently form water soluble moieties. The hydrophilic lubricants useful herein include polyalkylene glycols, alkoxy polyalkylene glycols, copolymers of methylvinyl ether and maleic acid, poly(vinylpyrrolidone), poly(acrylamide) including poly(N-alkylacrylamide), poly(acrylic acid), poly(saccharide), poly(vinyl alcohol), poly(ethyleneimine), polyamides, methyl cellulose, carboxymethylcellulose, polyvinylsulfonic acid, heparin, dextran, modified dextran, chondroitin sulphate, lecithin, and so forth. The polymers are typically chain-structured, non-crosslinked and water soluble having a hydrophilic group such as —OH, —CONH$_2$, —COOH, —NH$_2$, —COO—, —SO$_3$, —NR$_3^+$ and so forth where R is alkyl or hydrogen.

Derivatives of these polymers may also be utilized providing, even if they are not water soluble, that they are still of a structure which is capable of being hydrated, or is dispersible in water. Examples include esterified polymers, salts, amides, anhydrides, halides, ethers, hydrolyzates, acetals, formals, alkylols, quaternary polymers, diazos, hydrazides, sulfonates, nitrates, and ion complexes which are obtained by condensation, addition, substitution, oxidation, or reduction reactions of the above mentioned water soluble polymers. Also useful are polymers crosslinked with substances having more than one reactive functional group such as diazonium, azide isocyanate, acid chloride, acid anhydride, imino carbonate, amino, carboxyl, epoxy, hydroxyl and aldehyde groups. Further polymers include those copolymerized with vinyl, acrylic acid, methacrylic acid, diene compounds, and so forth.

A preferred class of hydrophilic lubricants are polyalkylene glycols or alkoxy polyalkylene glycols which have the following general formula:

R1 and R2 may be the same or different and can be H or an alkyl group having 1 to about 6 carbon atoms; x is from 2 to about 500; and y is from 0 to about 100.

The polyalkylene glycols and alkoxy polyalkylene glycols may also contain functional groups such as, for example, hydroxyl, sulfur, nitrogen or oxygen.

In a more specific preferred embodiment of the present invention, the water soluble lubricants are copolymers of polyalkylene glycols or alkoxy polyalkylene glycols. Specific examples of such copolymers include Pluronic® 31R1 surfactant, a polyoxypropylene/polyoxyethylene block copolymer available from BASF Corp. in Mount Olive, N.J. and Cremophor® EL 35, an ethoxylated castor oil (PEG 35 Castor Oil) or polyoxyethyleneglycerol triricino available from BASF Corp. in Wyandotte, Mich.

Alternatively, the lubricious coatings can be formed from hydrophobic compounds which can be converted to a lubricious hydrophilic compound through a chemical reaction such as hydrolysis, for instance. The conversion may take place once the coating process is complete. Examples of such compounds include those compounds having pendant ester or amide groups, such as, for instance, esters such as poly(acrylates), poly(meth)acrylates, poly(vinyl esters), poly(maleates), poly(fumerates), polyamides, poly(acrylamides), and copolymers and terpolymers thereof, and so forth. The poly(acrylic), poly(methacrylic) or polymaleic esters, and the polyamides or poly(acrylamides) may be converted to carboxylic acids by hydrolysis. Hydrolysis may be basic or acidic, and heat may be added to increase the rate of reaction. Esters are hydrolyzed reversibly in the presence of acid or irreversibly in the presence of base. The use of a large excess of water in the acid-catalyzed reaction favors hydrolysis. Vinyl esters may also be converted to an alcohol through saponification using an alkali-metal hydroxide which forms the alcohol and the metal salt of the acid. While most of these materials are hydrophobic, some are hydrophilic and can be hydrolyzed as well.

The following reaction schemes illustrate this embodiment of the present invention:

poly(vinyl acetates)

polyethylene-alt-maleic esters

R, $R_1$, $R_2$ and $R_3$ can each independently be hydrogen or alkyl having from one to four carbon atoms and n is an integer. The molecular weight range for these polymers is broad and may be from about 800 to about 400,000 g/mole. Preferably, the molecular weights are from about 1,000 to about 20,000 g/mole.

The main benefit of utilizing a water soluble lubricant is that it will quickly dissolve into the blood stream and move out of the body within a short period, reducing the likelihood of inflammation and restenosis. In contrast, the silicone based lubricants have been known to cause tissue reaction, irritation and inflammation in patients. Further, the water soluble lubricants of the present invention exhibit excellent lubricity and friction reduction. Oil based lubricants such as silicones, glycerine or olive oil tend to bead and migrate from the coated surface, reducing the benefits of the lubricant which may result in a surface that does not have as much lubricity and friction reduction. Furthermore, the lubricant then may move into the bloodstream where it has less compatibility than the water soluble lubricants resulting in irritation of tissue.

Various solvents and their mixtures may be useful as the carrier of the lubricant. Preferably, the solvents are polar and include alcohols, glycols, water and so forth. Specific examples include ethanol, methanol, isopropyl alcohol (IPA), stearyl alcohol, ethylene glycol, propylene glycol, glycerin, water, methylethyl ketone (MEK) and so forth. However, isopropanol and mixtures of isopropanol with other solvents, is preferred.

The lubricious coating may also contain Vitamin E which acts as an antioxidant. This improves the long term stability of the coating by reducing the degradation, allowing longer shelf stability. It is important that the lubricity of the medical device remains for an extended period to allow for the fact that such devices may not be used for a period of time. Vitamin E is sold in as a liquid and in itself has limited lubricious qualities and does not improve the overall lubricity of the coating. Vitamin E may be purchased from Sigma. Preferably, it will have a 95% purity or greater.

Preferably, the polymeric surface to be coated with the water soluble lubricants of the present invention will be surface primed with a crosslinkable primer composition. The hydrophilic coating, is relatively soluble in bodily fluids and can be easily washed away or flushed from the surface. Premature departure of the hydrophilic coating from the surface of the device may lead to insufficient lubricity. It is therefore desirable to retain the hydrophilic coating on the surface for a period of time. The primer acts to promote adhesion of the hydrophilic coating to the surface of the device thereby preventing premature removal of the lubricious coating.

The crosslinkable primer is generally hydrophobic in nature but has some substituents attached thereon that make it attractive to a hydrophilic polymer. It is surmised that the hydrophilic polymer adheres through hydrogen bonding. Therefore, any groups which participate in hydrogen bonding with the hydrophilic polymer will improve retention on the surface of the medical device.

The crosslinkable compounds include those having hydrophilic functionality such as amine, amide, carboxyl, hydroxyl, thiol, phosphorous, and so forth. The reactive primer is oriented in such a way that these functional groups provide a mechanism by which the water soluble lubricious coating may better adhere to the surface to be lubricated, thereby preventing the water soluble lubricious coating from immediately, or in any event prematurely, washing away upon exposure to bodily fluids, for instance.

A preferred class of crosslinkable composition for use in pretreating the surface of the medical device are crosslinkable silicones, such as silane or silicone oligomers. However, other crosslinkable chemical agents may be utilized as well, providing that they contain substituents to form hydrogen bonding with the hydrophilic polymer. It is possible, and preferable, to utilize only a small amount of silicone for this purpose, reducing the possibility of irritation to sensitive tissues. Furthermore, because the silicone compound utilized in the present invention crosslinks, it tends to adhere better to the polymeric surface thereby further reducing the likelihood that any irritation will occur due to the silicone based compound. This silicone primer provides a an excellent foundation for the lubricious coating, thereby improving both uniformity of the lubricious coating and the long term stability. This stability ensures that there will be lubrication even after a relatively long shelf life.

In a preferred embodiment of the present invention, a silane having amino groups is utilized to adhere the hydrophilic polymer on the surface, thereby improving the retention of the lubricious coating on the device.

More specifically, an example of a crosslinkable silicone surfactant useful to the present invention is a liquid silicone rubber elastomer, amino-functional polydimethylsiloxane, sold under the tradename of Silastic® MDX4-4210.

Other crosslinkable chemical compounds useful herein include titanate and zirconate coupling agents, such as isopropyl triisostearoyl titanate and neopentyl diallyl oxytri-neodecanoyl zirconate. Both are available in liquid form.

These crosslinkable agents are often supplied in a solution with heptane and its mixtures, being a preferred solvent. These agents may be put in solution alone, and then coated on the medical device prior to application of the hydrophilic coating, or they may be put in solution with the hydrophilic coating by using a cosolvent mixture, therefore eliminating one step in the coating process.

The lubricious coatings of the present invention may be utilized on any medical device wherein it is desirable to reduce the surface friction or adhesion between two surfaces, whether it be polymeric to polymeric surface or polymeric to metallic surface. Such medical devices include, but are not limited to, over the wire catheters, single operator exchange or rapid exchange catheters, fixed wire catheters, IV or over the needle catheters, introducing sheaths, Rotablator®, non-invasive surgical cutting devices, needles, blades, cannulas, any stent deployment device, and so forth. Catheters may be utilized to deploy an medical devices such as a stent, stent-graft, graft or vena cava filter to a precise location within a bodily lumen. Such deployed devices may be expandable or self-expandable devices. Over the wire catheters and rapid exchange catheters are discussed in detail in U.S. Pat. No. 5,534,007 to St. Germain et al. issued Jul. 9, 1996, incorporated herein by reference.

While it is preferable to the present invention that the inner surface of a tubular member be coated, the present invention is useful on any surface for which it is desired to reduce friction between that surface and another, second surface.

In a preferred embodiment of the present invention, the coating is utilized on a catheter assembly in which there is typically a first tubular member or outer sheath which forms a lumen within which other tubular members or metal wires may be housed. The outer sheath is made up of a distal portion and a proximal portion. Typically, the tubular member will be a thermoplastic polymeric material which is capable of being molded into a shaped article such as a hollow tube. Such materials may include, but are not limited to, homopolymers, copolymers and terpolymers of ethylene; homopolymers, copolymers and terpolymers of propylene; polyesters; polyamides; polyurethanes; vinylic copolymers; block copolymers; and so forth. For instance, materials as Nylon, Selar®, polyether-polyester block copolymers (i.e. Hytrel®), Pebax®, Surlyn®, polyethylene terephthalate, polytetrafluoroethylene, polyvinyl chloride, polyurethanes, polyetherurethanes, polyesterurethanes, polyurethane ureas, polyurethane siloxane block copolymers, polyethylene, polypropylene or other similar extrudable thermoplastic, polymeric materials, or composites thereof may be utilized in the present invention. Typically, a catheter may have a proximal end and a distal end, each of which is formed from a different material. It may, therefore, be two separate sheaths which are adhered together. The proximal end of the tubular sheath is typically made of a more flexible material than is the distal end. However, the entire sheath, both proximal and distal end, may be comprised of one material thereby forming a continous sheath. Such materials are typically inherently non-lubricious.

The lumen of the outer sheath may comprise other tubular members which may serve to transport fluids, to protect guide wires or pull back wires, or the lumen may contain the guidewires or pull back wires themselves. Both during deployment of the medical device, and during retraction, it will be necessary to reduce the adhesion or friction which may be present between the materials. As discussed in U.S. Pat. No. 5,534,007 and incorporated herein by reference, the outer sheath may be a flexible tube which contains a pull wire lumen and a guide wire lumen. The outer sheath is comprised of high density polyethylene (HDPE) or Surlyn®. Optionally, the outer sheath may enclose an optional guide wire lumen which is made of a flexible, but incompressible construction, such as a polymer encapsulated braid or coil which may be comprised of stainless steel or nitinol encased in a polymer such as a polyimide, HDPE, teflon or polyurethane. The lubricious coating of the present invention may be coated on both the inner surface of the outer sheath to reduce adhesion and friction between the guide wire lumen and the inner surface of the outer sheath, and on the inner surface of the guide wire lumen to reduce friction between the inner surface of the guide wire lumen and the guide wire itself.

In another preferred embodiment of the present invention, a tubular member having an inner surface and an outer surface and comprised of a thermoplastic polymeric material slides over a metal wire. The inner surface of the tubular member is coated with the lubricious coating of the present invention to reduce the adhesion and friction between the polymeric material and the metal when the metal wire is moved through the polymeric tube. With the lubricious hydrophilic coating of the present invention, it is possible to achieve up to a 65%, preferably at least about 30% and more preferably at least about 50%, reduction in force for the wire movement friction.

A further benefit to utilizing the coating of the present invention is that the radius of the tubular members may be reduced, thereby reducing the profile of the catheter and improving the traceability.

The surface of the tubular member may be primed or pre-treated with the reactive compound having hydrophobic and hydrophilic functionality thereon including those compounds having groups such as amine, amide, carboxyl, hydroxyl, and so forth. These groups are available on the surface for "binding" the water soluble lubricious coating in such a way that the coating will not wash away from the surface of the article. This reactive primer provides a uniform wettable surface which facilitates adherence of the lubricious coating along the elongated interior surface of the tube. The reactive compound may be silane or silicone oligomer which forms a crosslinked coating on the tubular surface upon application and drying. One method of treating priming or treating the inner surface of a tubular member involves a flush method whereby a solution of the lubricious coating is connected to a port of the tube via a syringe, and solution is thereby injected and passes through the entire tube. The silicone compound is dissolved in a solvent, preferably heptane or the like in a concentration of about 0.1% to about 10% of the crosslinkable compound, preferably from about 0.2% to about 5% concentration based on weight/volume. The excess solution trapped in the tubular member is removed through air pressure or nitrogen at 1–2 atmospheres. The crosslinking reaction is then carried out with heat at temperatures of about 30° C. to about 80° C., preferably from about 40° C. to about 65° C. and even more preferably at temperatures of about 45° C. to about 55° C.

The lubricious coating is prepared by making a solution of the water soluble lubricant in solvent at a concentration of about 1% to about 30% of the lubricant. Antioxidant may be added in an amount of about 0.01% to about 1.0% and preferably about 0.1% to about 0.5%. A preferable solvent is isopropanol. The lubricious coating may then be applied utilizing a flush method. A syringe may be connected to a port of the tubular member, the solution injected via a syringe or the like until approximately 3 mls passes through the tube. The lubricated tube is cleaned using air pressure or nitrogen at 1–2 atmospheres for at least 10 minutes, thereby removing excess solution.

Alternatively, the lubricious coating may be coextruded with the material from which the tubular member is being formed, such as polyethylene, Pebax®, polyester elastomer, and so forth, thereby forming a coating in this fashion. It is preferable that the lubricious coating be coextruded on the inside surface of the now dual layer tube.

In a preferred embodiment of the present invention, a hydrophobic ester is coextruded on the inside of the tubular member. The ester is subsequently hydrolyzed using an acid or base and heat, to form the hydrophilic lubricious coating on the inner surface of the tubular member.

EXAMPLES

Primer 1

A solution of crosslinkable silicone primer was prepared by dissolving 0.5 g of Silastic® MDX4 from Dow Corning Chemicals in Midland, Mich. in about 99.7 milliliters of heptane in a 100 ml column (concentration of 0.5% based on weight/volume). Silastic® MDX4 has a 50% concentration in a pseudocumene and isopropanol mixture as purchased. Heptane was purchased from Aldrich chemical in anhydrous form >99% purity with a water content of <0.005%. ps Primer 2

A solution of crosslinkable silicone was prepared by dissolving about 0.2 g of MDX4 in heptane. The MDX4 was weighed in a 100 ml column with a cap and heptane is added to total 100 ml (about 0.2% concentration based on weight/volume).

In each example the inner surface of a catheter was treated with the MDX4 using a flush method. A 20 ml glass syringe containing 10 ml of MDX4 solution was connected with the port of the catheter and 3 ml of solution is injected and passed through the whole catheter. The syringe was then moved to the other port. The treated catheter was then cleaned by air pressure or nitrogen at 1–2 atmospheres for in excess of 10 minutes to remove the excess solution trapped in the catheter. The cleaned catheter was then heated in an oven at 55° C. for at least 4 hours to carry out the crosslinking reaction.

Primer 3

A 3% weight/volume concentration of MDX4 to heptane was prepared as above.

Lubricious Coating 1

A solution of lubricant was prepared by dissolving 20 g of Pluronic® 31R1, polyoxypropylene-polyoxyethylene block copolymer from BASF and 0.02 g Vitamin E from Sigma in isopropanol (IPA) until a total of 100 ml is achieved resulting in a 20% weight/volume concentration. The IPA may be purchased from Aldrich Chemicals with >99% purity and a water content of <0.005%.

Lubricious Coating 2

A 10% solution of lubricant was prepared by dissolving 10 g of Pluronic® 31R1, 0.02 g Vitamin E in IPA until the total is 100 ml.

Lubricious Coating 3

A 20% solution of Cremophor® EL 35, ethoxylated castor oil, from BASF Corp. was prepared by dissolving 20 g of Cremophor® and 0.02 g Vitamin E in IPA until the total is 100 ml.

Lubricious Coating 4

A 20% solution of Cremophor® EL 35, ethoxylated castor oil, from BASF Corp. was prepared by dissolving 20 g of Cremophor® and 0.02 g Vitamin E in IPA until the total is 100 ml.

The inner surface of a catheter was lubricated using the flush method by connecting a 20 ml glass syringe containing about 10 ml lubricant solution to the port of the catheter, injecting the lubricant solution and passing it through the tip until 3 ml of solution was used. The catheter was then cleaned using air pressure or nitrogen gas at about 1–2 atmospheres for in excess of 10 minutes to remove any excess solution trapped in the catheter. The catheter is then heated to about 55° C. for about 1–2 hours and is conditioned over night at ambient temperature to ensure complete drying of the catheter.

Lubricious Coating 5

A 40% solution of Pluronic® 31R, polyoxypropylene-polyoxyethylene block copolymer from BASF, was prepared in isopropanol.

Example 1

A high density polyethylene balloon catheter with a lumen having an inner diameter of 0.0167" (0.0424 cm) was pretreated with Primer 1 followed with Lubricious Coating 3, above. Using a syringe, the lumen was then flushed with 3 mls of saline using a syringe. A stainless steel wire having an outer diameter or 0.0162" (0.0411 cm) was inserted and the wire movement force was measured using a computer controlled force test machine with a special fixture to model the tortuous shape of the coronary vessel. The wire was pulled at a rate of 8.25 mm/sec over a minimum of 300 mm. The test was done at ambient temperature. The force required to pull the wire through the catheter lumen was measured on the test specimen and on a control catheter which had no hydrophilic coating. The force required on the uncoated specimen was 250 g while that on the coated catheter was 85 g. A force reduction of 65% was noted.

Figure 1:
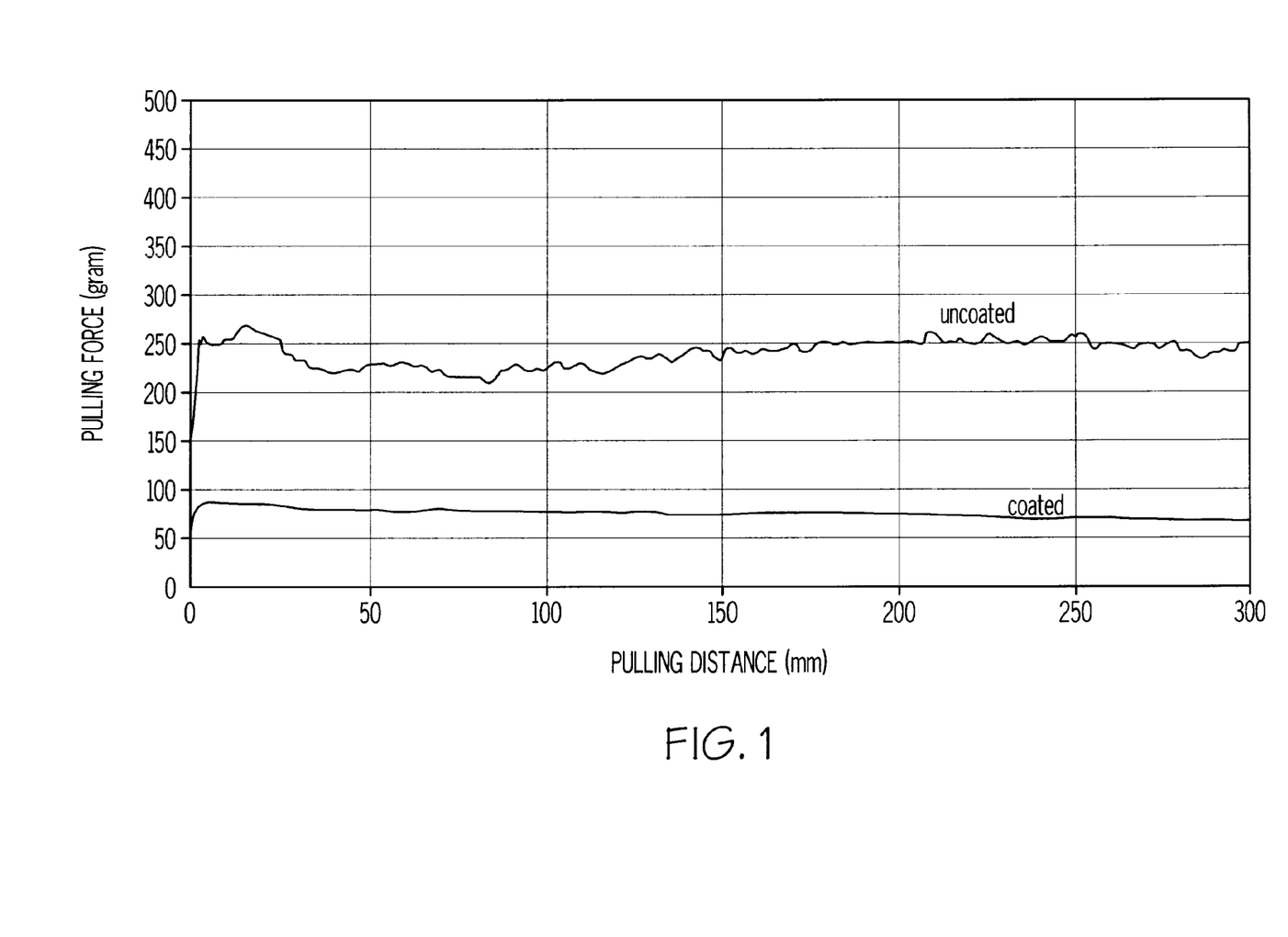
FIG. 1 illustrates the reduction in the wire movement frictional force achieved for Example 1 using the lubricious coating method of the present invention.

FIG. 1 illustrates the force required for the uncoated control catheter and for Example 1.

Example 2

A high density polyethylene balloon catheter having a lumen with an inner diameter of 0.0169" (0.0429 cm) was pretreated with Primer 2 followed by Lubricious Coating 1. The same procedure utilizing the same size wire as in Example 1 was followed. The uncoated catheter had a wire movement force of 60 g while the coated catheter had a wire movement force of 30 g. A 50% force reduction was achieved.

Figure 2:
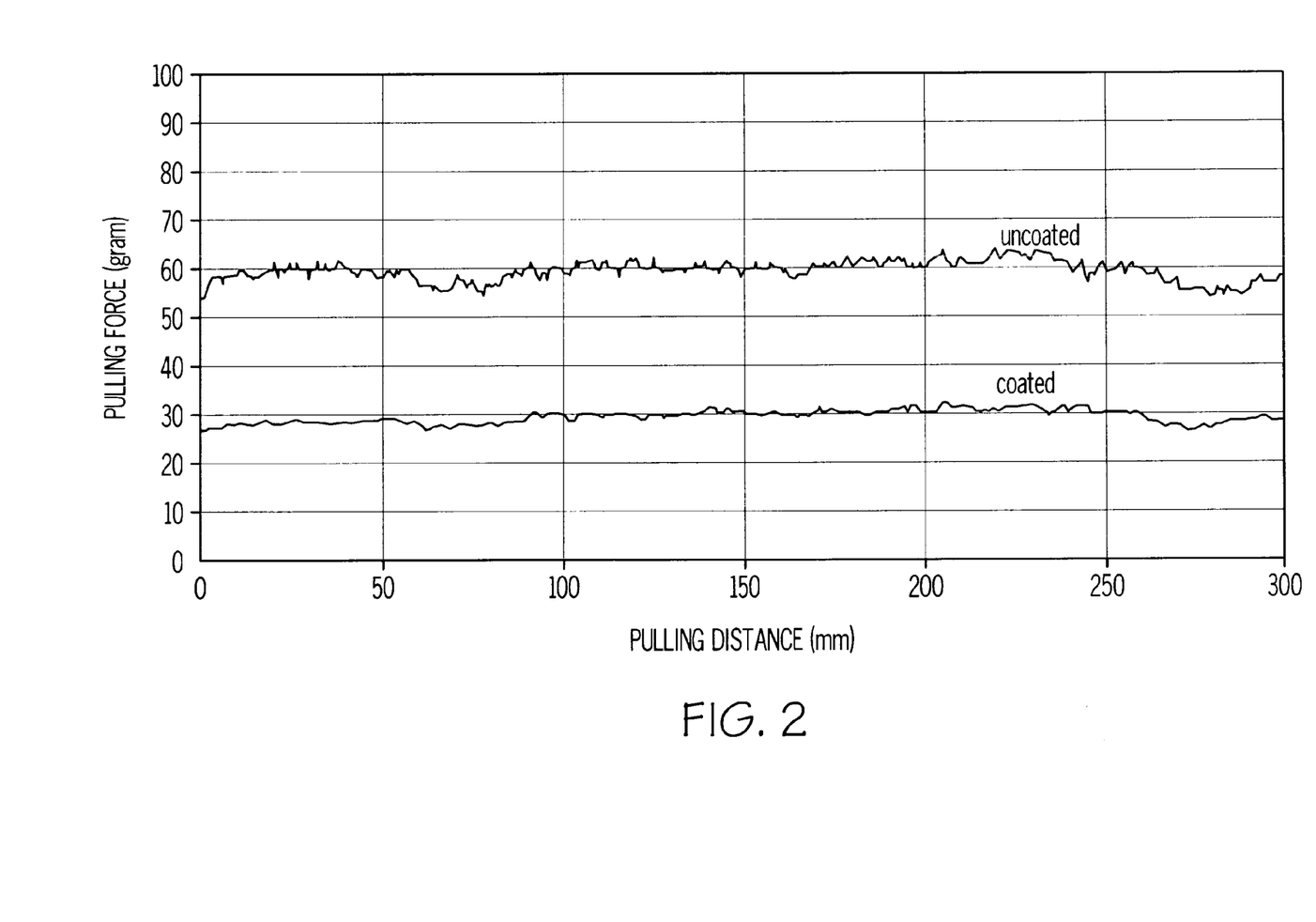
FIG. 2 illustrates the reduction in the wire movement frictional force achieved for Example 2 using the lubricious coating method of the present invention.

FIG. 2 illustrates the force required for the uncoated control catheter and for Example 2.

Example 3

A polyethylene tube with a length of 75 mm, an inner diameter of 1.27 mm, an outer diameter of 1.31 mm and a wall thickness of 0.2 mm was first coated with Primer 3. The tube was dried in an oven at 55° C. for 2 hours. The tube was then coated a second time with Lubricious Coating 5 and dried in an oven at 55° C. for over 2 hours to ensure complete drying. A stainless steel rod having a length of 75 mm and a diameter of 1.27 mm was inserted into the coated polyethylene tube to a length of 25 mm.

A control sample was prepared by coating a polyethylene tube as described above with Primer 3 and followed by a 6% concentration of DC 360 silicone lubricant. A stainless steel rod was also inserted into this tube.

A pull test using an Instron Force Tested to measure the force, in grams, required to remove the stainless steel rod from the polyethylene tube was performed on both test specimens. The specimen with the DC 360 lubricant exhibited a pull force of 1.58 lbs (~720 g) while the specimen with Lubricious Coating 5 exhibited a lower pull force of 1.04 lb (~470 g), illustrating the superiority of the coating of the present invention.

What is claimed is:

1. A medical device comprising at least one tubular member having an inner surface and an outer surface wherein said inner surface of said tubular member is at least occasionally subjected to contact with at least one second surface, said tubular member comprising a hydrophilic coating disposed on said inner surface of said tubular member, wherein said hydrophilic coating is present to reduce the friction between the inner surface of said tubular member and said second surface caused by movement, and said inner surface of said tubular member is pretreated with a crosslinkable primer composition.

2. The medical device of claim 1 wherein said tubular member comprises a thermoplastic polymeric material.

3. The medical device of claim 1 wherein said tubular member comprises at least one material selected from the group consisting of homopolymers, copolymers and terpolymers of ethylene; homopolymers, copolymers and terpolymers of propylene; polyesters; polyamides; polyurethanes; vinylic copolymers; block copolymers; block copolymer ionomers; and mixtures thereof.

4. The medical device of claim 1 wherein said at least one second surface comprises at least one material selected from the group consisting of polymeric materials, metals and mixtures thereof.

5. The medical device of claim 1 wherein said hydrophilic coating comprises at least one material selected from the group consisting of polyalkylene glycols; alkoxy polyalkylene glycols; poly(saccharide); poly(vinylpyrrolidone); poly (vinyl alcohol); poly(acrylic acid); poly(acrylamide); poly(maleic anhydride); copolymers thereof and mixtures thereof.

6. The medical device of claim 1 wherein said surface is pretreated with a crosslinkable surface modifying layer.

7. The medical device of claim 1 wherein said crosslinkable silicone is amino-functional polydimethylsiloxane.

8. The medical device of claim 1 wherein said crosslinkable primer composition is utilized at a concentration from about 0.1 to about 10%.

9. The medical device of claim 6 wherein said inner hydrophilic coating is formed by injecting a hydrophobic compound into said tubular member thereby forming a hydrophobic coating on said inner surface of said tubular member, and subsequently converting the surface of said hydrophobic coating to a hydrophilic coating.

10. The medical device of claim 9 wherein said hydrophobic compound is a polymer selected from the group consisting of poly(acrylates), poly(meth)acrylates, poly(vinyl esters), poly(maleate) esters, poly(fumerate) esters, polyamides, poly(acrylamides), copolymers and terpolymers thereof, and mixtures thereof.

11. The medical device of claim 9 wherein said hydrophobic polymer is converted to a carboxylic acid by hydrolysis.

12. The medical device of claim 1 wherein said hydrophilic lubricious coating further comprises Vitamin E.

13. The medical device of claim 1 coated by the process of:
 a) pre-treating said inner surface of said tubular member with a crosslinkable primer composition; and
 b) coating said inner surface of said pre-treated tubular member with a water soluble lubricious coating.

14. The medical device of claim 13 wherein said pre-treating (a), and said coating (b) are accomplished by means of a flushing method.

15. The medical device of claim 1 wherein said tubular member comprises a polymeric tube and said at least one second surface is a metallic wire.

16. The medical device of claim 15 wherein the friction is reduced between said inner surface of said tubular member and said at least one second surface by at least about 30%.

17. The medical device of claim 1 wherein said medical device is a catheter assembly.

18. The catheter assembly of claim 17 wherein said catheter is selected from the group consisting of fixed wire catheters, over the wire catheters and rapid exchange catheters.

19. The catheter assembly of claim 17 wherein said catheter is a stent deployment catheter.

20. The catheter assembly of claim 17 wherein said inner surface is a polymeric material and said at least one second surface is a metal wire.

21. The catheter assembly of claim 17 wherein said catheter is utilized to deploy a medical device selected from the group consisting of a stent, a stent-graft, a graft and a vena cava filter.

22. The catheter assembly of claim 17 wherein wire movement friction is reduced by greater than about 30%.

23. A stent deployment catheter assembly comprising:
 a. at least one tubular member for retention and release of a stent selected from the group consisting of a retractable sheath and at least one stent retaining sleeve wherein said tubular member has an inner surface and an outer surface wherein said inner surface comprises a hydrophilic, lubricious, coating; and
 b. a stent;
 wherein said inner surface of said tubular member is at least occasionally subjected to contact with said stent and said hydrophilic coating reduces friction between said inner surface of said tubular member and said stent.

24. The catheter assembly of claim 23 wherein said hydrophilic coating comprises at least one compound selected from the group consisting of polyalkylene glycol; alkoxy polyalkylene glycol; poly(saccharide); poly(vinylpyrrolidone); poly(vinyl alcohol); poly(acrylic acid); poly(acrylamide); poly(maleic anhydride); copolymers and mixtures thereof.

25. The catheter assembly of claim 23 wherein said inner surface of said tubular member is pretreated with a reactive primer composition.

26. The catheter assembly of claim 25 wherein said reactive primer composition comprises at least one crosslinkable silicone.

27. The catheter assembly of claim 26 wherein said silicone comprises amino groups.

28. The catheter assembly of claim 25 wherein said primer composition comprises at least one hydrophobic compound which is capable of undergoing a chemical reaction whereby said hydrophobic surface of said inner surface of said tubular member is converted to a hydrophilic lubricious coating.

29. The catheter assembly of claim 28 wherein said hydrophobic compound is a polymer selected from the group consisting of poly(acrylates), poly(meth)acrylates, poly(vinyl esters), poly(maleate) esters, poly(fumerate) esters, polyamides, poly(acrylamides), copolymers and terpolymers thereof, and mixtures thereof.

30. The catheter assembly of claim 28 wherein said primer composition comprises at least one hydrophobic polymer which is capable of forming a carboxylic acid through hydrolysis.

31. The catheter assembly of claim 23 wherein said stent is a tubular, flexible, expandable stent.

32. A medical device for insertion into the body, comprising a first surface which is at least periodically subjected to contact with a second surface; said first surface, comprising:
 a) a crosslinkable silicone primer having substituents capable of forming hydrogen bonds; and
 b) a lubricious, biocompatible hydrophilic polymer; wherein said crosslinkable silicone primer improves retention of said hydrophilic polymer to said polymeric surface, and said hydrophilic polymer reduces friction between said first polymeric surface and said second surface.

33. A method of forming a lubricious hydrophilic coating on the inner surface of a tubular member comprising the steps of:
 a) coextruding a first hydrophobic polymer simultaneously with a second hydrophobic polymer wherein said first and second polymers form a tubular member having a first inner hydrophobic surface formed from said first hydrophobic polymer and a second outer hydrophobic surface formed from said second polymer; and
 b) converting said first inner hydrophobic surface to a lubricious hydrophilic surface.

34. A method of forming a lubricious hydrophilic coating on the inner surface of a tubular member comprising the steps of:
 a) coextruding a first hydrophobic polymer simultaneously with a second hydrophobic polymer wherein said first and second polymers form a tubular member having a first inner hydrophobic surface formed from said first hydrophobic polymer and a second outer hydrophobic surface formed from said second polymer; and b) converting said first inner hydrophobic surface to a lubricious hydrophilic surface.

35. The catheter assembly of claim 1 wherein said primer composition includes a titanate, a zirconate, or a mixture thereof.

36. A medical device comprising at least one tubular member having an inner surface and an outer surface wherein said inner surface of said tubular member is at least occasionally subjected to contact with at least one second surface, said tubular member comprising a hydrophilic coating disposed on said inner surface of said tubular member, wherein said hydrophilic coating is present to reduce the friction between the inner surface of said tubular member and said second surface caused by movement, and said inner surface of said tubular member is pretreated with a primer compound comprising substituents that improve the retention of said hydrophilic coating by hydrogen bonding.

37. The medical device of claim 36 wherein said substituents are selected from the group consisting of amine, amide, carboxyl, hydroxyl, thiol, phosphorous, and mixtures thereof.

38. The method of claim 33 wherein said converting step is accomplished through a chemical reaction.

* * * * *